(12) United States Patent
Staker

(10) Patent No.: US 9,671,344 B2
(45) Date of Patent: Jun. 6, 2017

(54) HIGH-DENSITY BIOCHEMICAL ARRAY CHIPS WITH ASYNCHRONOUS TRACKS FOR ALIGNMENT CORRECTION BY MOIRÉ AVERAGING

(75) Inventor: Bryan P. Staker, Pleasanton, CA (US)

(73) Assignee: Complete Genomics, Inc., San Jose, CA (US)

( * ) Notice: Subject to any disclaimer, the term of this patent is extended or adjusted under 35 U.S.C. 154(b) by 598 days.

(21) Appl. No.: 13/221,648

(22) Filed: Aug. 30, 2011

(65) Prior Publication Data

US 2012/0224050 A1    Sep. 6, 2012

Related U.S. Application Data

(60) Provisional application No. 61/378,844, filed on Aug. 31, 2010, provisional application No. 61/378,848, filed on Aug. 31, 2010.

(51) Int. Cl.
*G01N 33/00* (2006.01)
*G01N 21/64* (2006.01)
*B01J 19/00* (2006.01)
*C40B 20/02* (2006.01)

(52) U.S. Cl.
CPC ...... *G01N 21/6452* (2013.01); *B01J 19/0046* (2013.01); *C40B 20/02* (2013.01); *G01N 21/6458* (2013.01); *B01J 2219/00531* (2013.01); *B01J 2219/00659* (2013.01); *B01J 2219/00662* (2013.01); *B01J 2219/00693* (2013.01); *G01N 21/6428* (2013.01)

(58) Field of Classification Search
CPC . G01N 21/6452; G01N 21/6428; B01J 19/46; C40B 20/02
See application file for complete search history.

(56) References Cited

U.S. PATENT DOCUMENTS

| | | |
|---|---|---|
| 6,210,891 B1 | 4/2001 | Nyren et al. |
| 6,272,207 B1 | 8/2001 | Tang |
| 6,309,824 B1 | 10/2001 | Drmanac |
| 6,376,117 B1 | 4/2002 | Kantak et al. |
| 6,376,177 B1 | 4/2002 | Poponin |
| 6,396,995 B1 | 5/2002 | Stuelpnagel et al. |
| 6,401,267 B1 | 6/2002 | Drmanac |
| 6,537,801 B1 | 3/2003 | Ida et al. |

(Continued)

FOREIGN PATENT DOCUMENTS

WO    2012/031011 A1    3/2012

OTHER PUBLICATIONS

International Search Report and Written Opinion for PCT Patent Application No. PCT/US2001/50047 mailed on Jan. 5, 2012, 9 pages.

(Continued)

*Primary Examiner* — Sam P Siefke
(74) *Attorney, Agent, or Firm* — Kenneth R. Allen; J. Michael Schiff; Kilpatrick Townsend & Stockton LLP

(57) ABSTRACT

An array chip useful for biochemical assays is provided wherein the chip includes a field region arranged with attachment sites according to a first pitch and at least one track region having a one-dimensional spot pattern arranged according to a second pitch that is less dense and is a non-integer multiple of the first pitch so that one-dimensional Moiré averaging may be applied in the track region, thereby to attain alignment of the chip to the optical instrumentation with a higher density of attachment sites.

19 Claims, 7 Drawing Sheets

(56) References Cited

U.S. PATENT DOCUMENTS

| | | |
|---|---|---|
| 6,544,732 B1 | 4/2003 | Chee et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,070,927 B2 | 7/2006 | Drmanac |
| 7,072,500 B2 | 7/2006 | Cerrina et al. |
| 7,230,705 B1 | 6/2007 | Yang et al. |
| 7,422,911 B2 | 9/2008 | Schembri |
| 8,175,452 B1 | 5/2012 | Staker et al. |
| 8,298,768 B2 | 10/2012 | Drmanac |
| 8,445,194 B2 | 5/2013 | Drmanac |
| 8,774,494 B2 | 7/2014 | Staker |
| 2001/0038070 A1 | 11/2001 | Hausch et al. |
| 2002/0102578 A1 | 8/2002 | Dickinson et al. |
| 2003/0036067 A1 | 2/2003 | Schwartz |
| 2004/0253614 A1 | 12/2004 | Yonekawa et al. |
| 2007/0087362 A1 | 4/2007 | Church et al. |
| 2007/0207482 A1 | 9/2007 | Church et al. |
| 2008/0234136 A1 | 9/2008 | Drmanac et al. |
| 2008/0267022 A1 | 10/2008 | Bakker |
| 2009/0017197 A1 | 1/2009 | Zhang et al. |
| 2009/0155793 A1 | 6/2009 | Oliphant |
| 2009/0264299 A1 | 10/2009 | Drmanac et al. |
| 2011/0071053 A1 | 3/2011 | Drmanac et al. |
| 2014/0085457 A1 | 3/2014 | Staker et al. |

OTHER PUBLICATIONS

Bajcsy, Peter, "Gridline: Automatic Grid Alignment in DNA Microarray Scans", IEEE Transactions on Image Processing, vol. 13, No. 1, Jan. 2004, pp. 15-25.
Non-Final Office Action of Dec. 3, 2012 for U.S. Appl. No. 13/222,925, 13 pages.
"Viruses" (Wikipedia.com, accessed Nov. 24, 2012) 34 pages.
"How many species of bacteria are there" Wisegeek.com; accessed Sep. 23, 2011, 2 pages.
"Plant" (Wikipedia.com; accessed Mar. 8, 2013) 12 pages.
"Mammal" (Wikipedia.com; accessed Sep. 22, 2011) 17 pages.
"Murinae" (Wikipedia.com, accessed Mar. 28, 2013) 21 pages.
International Preliminary Report on Patentability for PCT Patent Application No. PCT/US2011/50047 mailed on Mar. 5, 2013, 7 pages.
Final Office Action of May 30, 2013 for U.S. Appl. No. 13/222,925, 22 pages.
Non-Final Office Action of May 9, 2014 for U.S. Appl. No. 14/090,529, 14 pages.
Gu Jian et al: "A new approach to fabricating high density nanoarrays by nanocontact printing", Journal of Vacuum Science and Technology: Part B, AVS / AIP, Melville, New York, NY, US, vol. 26, No. 6, Nov. 3, 2008 (Nov. 3, 2008), pp. 1860-1865, XP012114385, ISSN: 1071-1023, DOI: 10.1116/1.2998754.
Office Action of Apr. 23, 2015 for U.S. Appl. No. 14/090,529.
Beaucage et al., The Functionalization of Oligonucleotides via Phosphoramidite Derivative, Tetrahedron, vol. 49, No. 10,1993, pp. 1925-1963.
Letsinger et al., Effects of pendant groups at phosphorus on binding properties of d-ApA analogues, Nucleic Acids Research, vol. 14, 1986, pp. 3487-3499.
Letsinger et al., Phosphoramidate Analogs of Oligonucleotides, Journal of Organic Chemistry, vol. 35, No. 11, 1970, pp. 3800-3803.
Sprinzl et al., Enzymatic Incorporation of ATP and CTP Analogues into the 3' End of tRNA, EuroQean Journal of Biochemistry, vol. 81,, 1977, pp. 579-589.
Australian Application No. 2011295903, First Examiner Report mailed on Apr. 1, 2014, 3 pages.
Chinese Application No. 201180050914.3, Office Action, with English translation, mailed on Oct. 17, 2014, 4 pages. (Translation by Insight Intellectual Property Attorneys).
Chinese Application No. 201180050914.3, Office Action, with English translation, mailed on Feb. 7, 2014, 8 pages. (Translation by Insight Intellectual Property Attorneys).
Japanese Application No. 2013-527283, Office Action, with English translation, mailed on Mar. 8, 2016, 6 pages. (Translation by Yamakawa International Patent Office).
Japanese Application No. 2013-527283, Office Action, with English translation, mailed on Jul. 21, 2015, 10 pages. (Translation by Yamakawa International Patent Office).
U.S. Appl. No. 14/090,529, Non-Final Office Action mailed on Apr. 5, 2016, 22 pages.
U.S. Appl. No. 14/090,529, Restriction Requirement mailed on Mar. 6, 2014, 5 pages.

HIGH-DENSITY BIOCHEMICAL ARRAY CHIPS WITH ASYNCHRONOUS TRACKS FOR ALIGNMENT CORRECTION BY MOIRÉ AVERAGING

PRIORITY CLAIM; CROSS-REFERENCES TO RELATED APPLICATIONS

This application claims priority and benefit under 35 U.S.C. §119(e) from U.S. Provisional Patent Application No. 61/378,844, filed on Aug. 31, 2010 and entitled "HIGH-DENSITY BIOCHEMICAL ARRAY CHIPS", the entire contents of which is hereby incorporated by reference as if fully set forth herein; this application also claims priority and benefit under 35 U.S.C. §119(e) from U.S. Provisional Patent Application No. 61/378,848, filed on Aug. 31, 2010 and entitled "HIGH-DENSITY BIOCHEMICAL ARRAY CHIPS WITH SYNCHRONOUS TRACKS", the entire contents of which is hereby incorporated by reference as if fully set forth herein.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

This description relates to chemical array chips, particularly biochemical arrays, used for chemical analysis by optical techniques.

Array chips, such as those used in chemical and biochemical assays, allow large numbers of biochemical experiments to be performed in parallel. For example, a biochemical array chip may be part of a system for processing biochemical experiments in parallel. Array chips have solid, planar substrates made from silicon or glass wafers, or other materials. Biomolecules, reagents, fluorescent markers and other chemical compounds are applied to array chips in regular patterns.

Biochemical experiments may be performed on array chips by washing reagents over them according to precise protocols that specify chemical compounds and mixtures to be used, temperature, incubation time, and other parameters appropriate to a particular type of experiment.

In some operational contexts, biochemical experiments may be used along with fluorescence imaging to identify DNA bases—A, C, G, or T—by designing biochemical reactions such that a different colored dye (for example, red, green, blue, or yellow) corresponds to each one. For example, a fluorescence microscope or other suitable optical system may be used to take images of the biochemical experiments disposed and/or conducted on an array chip. The colors observed indicate the DNA bases at that particular experiment step. Extracting data from an array chip with such DNA experiments thus depends on recording the color of fluorescence emitted by many millions or even billions of biochemical experiments that may be present on the chip.

However, obtaining useful data from a fluorescence image of a dense biochemical array chip is complicated by competing interests of spatial resolution, accuracy, and speed. Images must be obtained at high enough magnification for individual experiments to be clearly resolved. At the same time images must cover a large enough field of view for experiments to be correctly identified. Finally, for large scale studies, imaging and image processing must take place quickly enough to provide for sufficient throughput and to make sequencing operations commercially feasible.

SUMMARY

Described herein are principles for, and various embodiments of, high-density array chips that address the competing interests involved in imaging and image processing of biochemical experiments disposed on the chips. For example, the high-density array chips described herein address the problem of how to achieve a very high density of biochemical experiments on the chips while at the same time allowing for rapid extraction of data from images of the chips. Further, the high-density array chips described herein also address the problem of how to provide for real-time alignment between an array chip and an imaging instrument that is used to take the images of biochemical experiments disposed on the chip during operation. As illustrated in the various embodiments and principles described herein, these problems are addressed by encoding information on an array chip in the form of one or more track regions that have different pitch and/or different density than other regions of the chip.

For example, the high-density array chips described herein provide for track regions that occupy a small percentage of the total area of the chips, while the rest of the chips' area is occupied by regions having a different and/or more dense array grid. Information encoded as one or more track regions of an array chip is used in operation to reduce the time necessary to align an imaging instrument (e.g., such as a fluorescence microscope camera) with the chip, while at the same time providing for real-time adjustment of such alignment. The real-time alignment of the imaging instrument is achieved by continuously monitoring for alignment errors based on information extracted from the images of the track region(s) on the array chip, and then correcting the alignment based on the alignment errors as the imaging instrument moves across the array chip and takes images of the biochemical experiments disposed thereon.

According to the principles and embodiments described herein, an array chip design, suitable for biochemical assays, is provided where the chip includes a field region arranged with attachment sites according to a first pitch and at least one track region having a one-dimensional spot pattern arranged according to a second pitch that is less dense and is a non-integer multiple of the first pitch so that so one-dimensional Moiré averaging can be applied in the track region, thereby to attain alignment of the chip to the optical instrumentation with a higher density of attachment sites.

In an example embodiment, a chip for assays comprises: a substrate comprising a field region and a track region; experiment sites disposed in a first patterned array in the field region, the first patterned array being defined by a first pitch; and alignment sites disposed in a second patterned array in the track region, the second patterned array being defined by a second pitch along a single dimension. The second pitch differs from the first pitch by a non-integer multiple in order to permit Moiré averaging-based alignment.

In one aspect of this embodiment, the field region has a density of one object space pixel per one experiment site. In another aspect, the field region has a density of two object space pixels per one experiment site, where the experiment sites in the field region are arranged in a checkerboard pattern. In yet another aspect, the field region has a density of four object space pixels per one experiment site.

In one aspect, the alignment sites in the track region are operative to support biochemical experiments. In another aspect, selected ones of the alignment sites are deleted in accordance with a preselected pattern. In yet another aspect, selected ones of the alignment sites are deleted in accordance with a pseudo-random pattern.

In one aspect, the experiment sites in the field region and the alignment sites in the track region are both configured to support biochemical experiments. In one aspect, the experiment sites in the field region and the alignment sites in the track region are configured to support attachment of DNA nanoballs.

In one aspect, the areas of the substrate of the array chip that are different than the experiment sites (in the field region) and the alignment sites (in the track region) are chemically treated to inhibit binding of target nucleic acids.

In one aspect the single dimension, along which the track region is disposed, is a horizontal dimension. In another aspect the single dimension is a vertical dimension.

In one aspect, the track region is separated from the field region by a site-free band. In another aspect, the size of the track region is one of: three times the size of an object space pixel, and five times the size of an object space pixel.

In one aspect, the substrate of the array chip further comprises a horizontal track region that is disposed substantially perpendicular to the vertical track region, where the horizontal track region comprises track sites disposed according to the second patterned array along a second dimension that is substantially perpendicular to the single dimension, along which the track region is disposed.

In an example embodiment, a method comprises: an imaging instrument taking an image of a chip on which target nucleic acids have been disposed, where the chip comprises: a substrate comprising a field region and a track region, experiment sites disposed in a first patterned array that is defined by a first pitch and that is disposed in the field region, and alignment sites disposed in a second patterned array that is defined by a second pitch along a single dimension and that is disposed in the track region, where the second pitch differs from the first pitch by a non-integer multiple and the target nucleic acids are attached to the experiment sites and the alignment sites; a correlation logic determining a correction alignment term for the single dimension by using, at least in part, Moiré averaging based on signals recorded in the image that are emitted from the target nucleic acids attached to the alignment sites in the track region; and automatically aligning the chip with the imaging instrument along the single dimension based on the correction alignment term.

In one aspect of this embodiment, the substrate of the chip further comprises a horizontal track region that is disposed substantially perpendicular to the vertical track region, where the horizontal track region comprises track sites disposed according to the second patterned array along a second dimension that is substantially perpendicular to the single dimension. In this aspect, the method further comprises: the correlation logic determining a second correction alignment term for the second dimension by using, at least in part, Moiré averaging based on signals recorded in the image that are emitted from the target nucleic acids attached to the track sites in the second track region; and automatically aligning the chip with the imaging instrument along the second dimension based on the second correction alignment term.

In one aspect of this embodiment, the step of the correlation logic determining the correction alignment term for the single dimension further comprises: as part of the correction alignment term, determining a track pitch misalignment error based at least in part on: the signals recorded in the image that are emitted from the target nucleic acids attached to the alignment sites in the track region, and information representing a pattern of deletion sites in the at least one track region.

In one aspect, the target nucleic acids attached to the chip comprise DNA nanoballs. In another aspect, a subset of the alignment sites in the track region are selectively deleted to form a pattern of deletions, and step of the correlation logic determining the correction alignment term further comprises computing the correction alignment term based at least in part on an ordered data set that represents the pattern of deletions.

The invention can be better understood by reference to the following detailed description in connection with the accompanying drawings.

DETAILED DESCRIPTION

Figure 1:
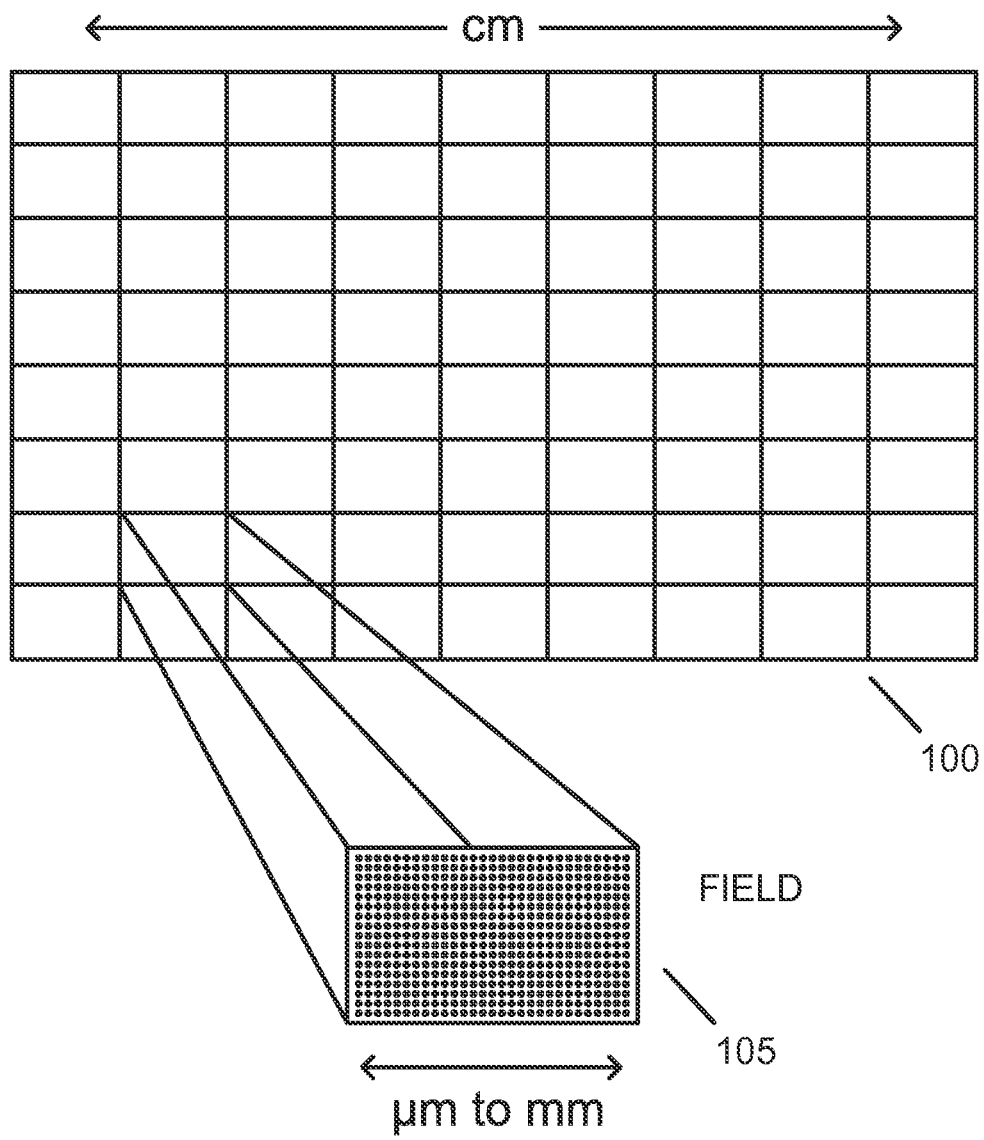
FIG. 1 is a top plan view of a portion of a high-density biochemical array chip with an inset illustrating an example pattern for field regions and track regions (size not to scale).

In the following description, for the purposes of explanation, numerous specific details are set forth in order to provide a thorough understanding of the present invention. It will be apparent, however, to the skilled in the art, that the present invention may be practiced without all or some of these specific details.

Selected Definitions

"Array chip" (or simply "chip") refers to a solid phase support (e.g., such as a substrate) having a surface, preferably but not exclusively a planar or substantially planar surface, that carries an array of sites to which nucleic acids or macromolecules can attach to form a biochemical assay. When attached to a site, the nucleic acids or macromolecules may be covalently bound to the solid support of the array chip, or may be non-covalently bound. Typically, the identities of the attached nucleic acids or macromolecules are not discernable, at least initially, from their site locations but may be determined by a particular operation on the array, such as by sequencing, hybridizing decoding probes, or the like. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Fluorophores" are any molecules comprising or consisting of a functional group that absorbs energy within a specific absorption spectrum and re-emits energy (e.g., such as light) at a different (but equally specific) emission spectrum. Preferred fluorophores for use as markers include, but are not limited to, fluorescein, cascade blue, hexachloro-fluorescein, tetrachloro-fluorescein, TAMRA, ROX, FAM, Cy3, Cy3.5, Cy5, Cy5.5, Texas Red, Eosin, the DyLight Fluor family available from Thermo Fisher Scientific of Waltham, Mass., and the Alexa Fluor family from Molecular Probes of Eugene, Oreg.

"Image space" refers to the area covered by the set of pixels in a camera, and "image space pixel" refers to a camera pixel.

"Logic" refers to a set of instructions which, when executed by one or more processors, are operable to perform one or more functionalities and/or return data in the form of one or more results. In various embodiments and implementations, any such logic may be implemented as one or more software components that are executable by one or more processors, as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone or client-server software application, as one or more software modules, as one or more libraries of functions, and as one or more static and/or dynamically-linked libraries.

"Macromolecule" used in relation to a nucleic acid means a nucleic acid having a measurable three dimensional structure, including linear nucleic acid molecules with comprising secondary structures (e.g., amplicons), branched nucleic acid molecules, and multiple separate copies of individual sequences with interacting structural elements, e.g., complementary sequences, palindromes, or other sequence inserts that cause three-dimensional structural elements in the nucleic acid.

"Nucleic acid", "oligonucleotide", "polynucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones, and non-ribose backbones. Modifications of the ribose-phosphate backbone may be done to increase the stability of the molecules; for example, PNA:DNA hybrids can exhibit higher stability in some environments.

"Object space" refers to the area of an object such as an array chip, and thus "object space pixel" refers to a unit of area on an object such as an array chip. The size of object space pixels is typically determined by the size of the image space pixels (i.e., camera pixels) and the magnification that is applied when the camera is used to take images of the object space. The magnification is the ratio of the size of an image space pixel (i.e., a camera pixel) to the actual size of the object space area that corresponds to the image space pixel as observed by the camera.

For example, a magnification of 16× allows a camera using 8 µm pixels to observe 500 nm object space pixels. In various embodiments, the size of an object space pixel may be between 200-1000 nm in width and 200-1000 nm length; in a preferred aspect the size of an object space pixel may be 320 nm by 320 nm, more preferably 600 nm by 600 nm, even more preferably 500 nm by 500 nm. In some embodiments, the size of an object space pixel is selected to be substantially the same as, or slightly bigger, than the size of a site on an array chip, so that only a single discrete site will fit into an object space pixel. This ensures that, in operation, the intensity of the energy (e.g., light) emitted from a site on the array chip can be recorded by a single camera pixel.

"Pitch" (also referred to as "period") refers to a uniform distance that defines a pattern such as, for example, an array. The pitch of an array chip, or a region thereof, refers to the uniform distance between the centers of any two adjacent sites disposed in an array grid on the chip, thereby defining the array of the chip, or the region thereof. The pitch of a camera refers to the uniform distance between the centers of any two adjacent camera pixels and defines the pixel array of the camera.

"Sequence determination" in reference to a target nucleic acid means determination of information relating to the sequence of nucleotides in the target nucleic acid. Such information may include the identification or determination of partial as well as full sequence information of the target nucleic acid. The sequence information may be determined with varying degrees of statistical reliability or confidence. In one aspect, the term includes the determination of the identity and ordering of a plurality of contiguous nucleotides in a target nucleic acid starting from different nucleotides in the target nucleic acid.

"Site" (also referred to as "spot") refers to a spatially defined area on an array chip that does not overlap with other sites on the chip; that is, the sites on an array chip are spatially discrete and may be arranged in a particular pattern. On an array chip, a site is typically configured to have dimensions (e.g., length, width, and possibly depth or height) that are suitable for the attachment of nucleic acids or macromolecule(s). Examples of sites include, but are not limited to, depressions, raised areas, micro-wells, beads, and the like.

"Target nucleic acid" means a nucleic acid (or a macromolecule thereof) from a gene, a regulatory element, genomic DNA (including, but not limited to, human DNA), cDNA, RNAs including mRNAs, rRNAs, siRNAs, miRNAs and the like, and fragments thereof. A target nucleic acid may be a nucleic acid from a sample, or a secondary nucleic acid such as a product of an amplification reaction.

Array Chip Imaging

Image-based techniques identify individual biochemical experiments on an array chip by the positions of the sites on which the experiments are disposed on the chip. For example, the intensity of the energy (e.g., such as light)

emitted from the sites is recorded as an image, and the image is then processed to determine the positions of the sites on the chip. A biochemical experiment may be identified by the coordinates of its site on the chip in a two-dimensional (e.g., X-Y), planar coordinate system, for instance. An image of an array chip typically includes a large enough area such that locations of the experiments' sites may be measured and/or computed with respect to the coordinate system in use. Some prior approaches use conventional alignment marks (e.g., such as cross etchings) for this purpose; however, drawbacks of such marks include difficulty of observing them with fluorescence microscopes, incompatibility of materials, and wasted chip area. In contrast, the high-density array chips described herein use the biochemical experiments themselves (arranged in specific patterns), and the energy emitted therefrom, to aid identification.

In various operational contexts, images of the biochemical experiments disposed on an array chip may be obtained with an imaging instrument that includes a camera attached to a fluorescence microscope. The magnification of the microscope determines how many biochemical experiment sites can be "seen" by a camera pixel at the one time; equivalently, the magnification determines the ratio of the size of a camera pixel (in image space) to the size of a chip area (in object space) that is observed and corresponds to the camera pixel. For example, a magnification of 16× allows a camera using 8 μm pixels to record signals from 500 nm chip areas (e.g., object space pixels). Thus, the rate at which data may be extracted from an array chip depends, in part, on how many camera pixels correspond to each spot on the chip (presuming that the size of a spot is smaller than the size of an object space pixel). For example, a one-megapixel camera operating at twenty camera pixels per spot can image 50,000 spots. If the same camera is operated with two (or even one) camera pixel per spot, the number of spots per image is ten (or twenty) times greater. While low pixel-to-spot ratios (e.g., such as 1:1, 2:1, and 4:1) are very desirable since they greatly increase imaging throughput, they also impose very demanding requirements on the alignment of the camera pixels with the array chip spots during operation.

According to the principles and embodiments described herein, carefully designed spatial patterns of sites for biochemical experiments on an array chip aid the accuracy and speed of data acquisition via fluorescence imaging. The specific layout principles described hereinafter enable rapid imaging of very high density biochemical arrays and thus improve the throughput of large scale imaging systems such as genome sequencing systems. Further, the described novel chip designs aid accuracy of chip alignment and identification while maximizing the area of the chip that can be used for biochemical experiment sites.

As described herein, precise alignment correcting for fractional offsets is achieved by correcting for errors in sub-pixel X-Y alignment by use of Moiré averaging. In Moiré averaging, magnification is intentionally set so that the period of the object space pixels corresponding to the pixels of the imaging element (e.g., a camera) is a non-integer multiple of the period that defines the sites in a track region of the chip. Accurate pixel-level alignment is achieved by providing for pre-defined and pseudo-randomly disposed sets of sites (herein referred to as deletion or reserved sites), on which biochemical materials are prevented from attachment to the chip substrate so that the deletion sites of the array can be used in a pattern matching scheme as registration markers for absolute location identification. Additional techniques for initial registration and subsequent correction of scale, rotation, and X-Y offsets for high-density array chips are described in: (1) U.S. patent application Ser. No. 13/092,618, filed on Apr. 22, 2011 and entitled "METHOD AND SYSTEM FOR ACCURATE REGISTRATION OF ARRAY FOR DNA SEQUENCING", the entire contents of which is hereby incorporated by reference for all purposes as if fully set forth herein; and (2) U.S. patent application Ser. No. 12/912,641, filed on Oct. 26, 2010 and entitled "METHOD AND SYSTEM FOR IMAGING HIGH DENSITY BIOCHEMICAL ARRAYS WITH SUB-PIXEL ALIGNMENT", the entire contents of which is hereby incorporated by reference for all purposes as if fully set forth herein.

High-Density Array Chips with Track Regions

Turning now to FIG. 1, a high-density biochemical array chip according to one embodiment is shown. Chip 100 is based on a solid, planar substrate and is conveniently dimensioned in several centimeters in length and width. Typical chip dimensions may be 2.5 cm by 7.5 cm by 0.1 cm, for example. Smaller chips (e.g. less than about 0.5 cm on a side) are possible but may be less convenient to handle in some operational contexts, and it may be difficult to maintain required flatness for larger chips (e.g., more than about 10 cm on a side). In some embodiments, chips designed according to the principles described herein may support more than one billion biochemical experiments. For example, in cPAL sequencing with DNA nanoballs (which is described in a separate section hereafter), each experiment is carried out within a circular area approximately 300 nm in diameter. In other embodiments, biochemical experiments may be carried out on chip sites that are between 30-1000 nm in diameter (or length and width), or even 200-500 nm in diameter (or length and width).

To break the imaging problem into manageable chunks, array chips are divided into micron-to-millimeter sized fields; e.g. field 105. In one embodiment, a typical field may be 500 μm by 500 μm; thus a typical chip is divided into hundreds or thousands of fields. In other embodiments, a field may be of sizes that are between 320-1600 μm by 320-1600 μm, 600 μm by 600 μm, or even 1.6 mm by 700 μm.

Figure 2:
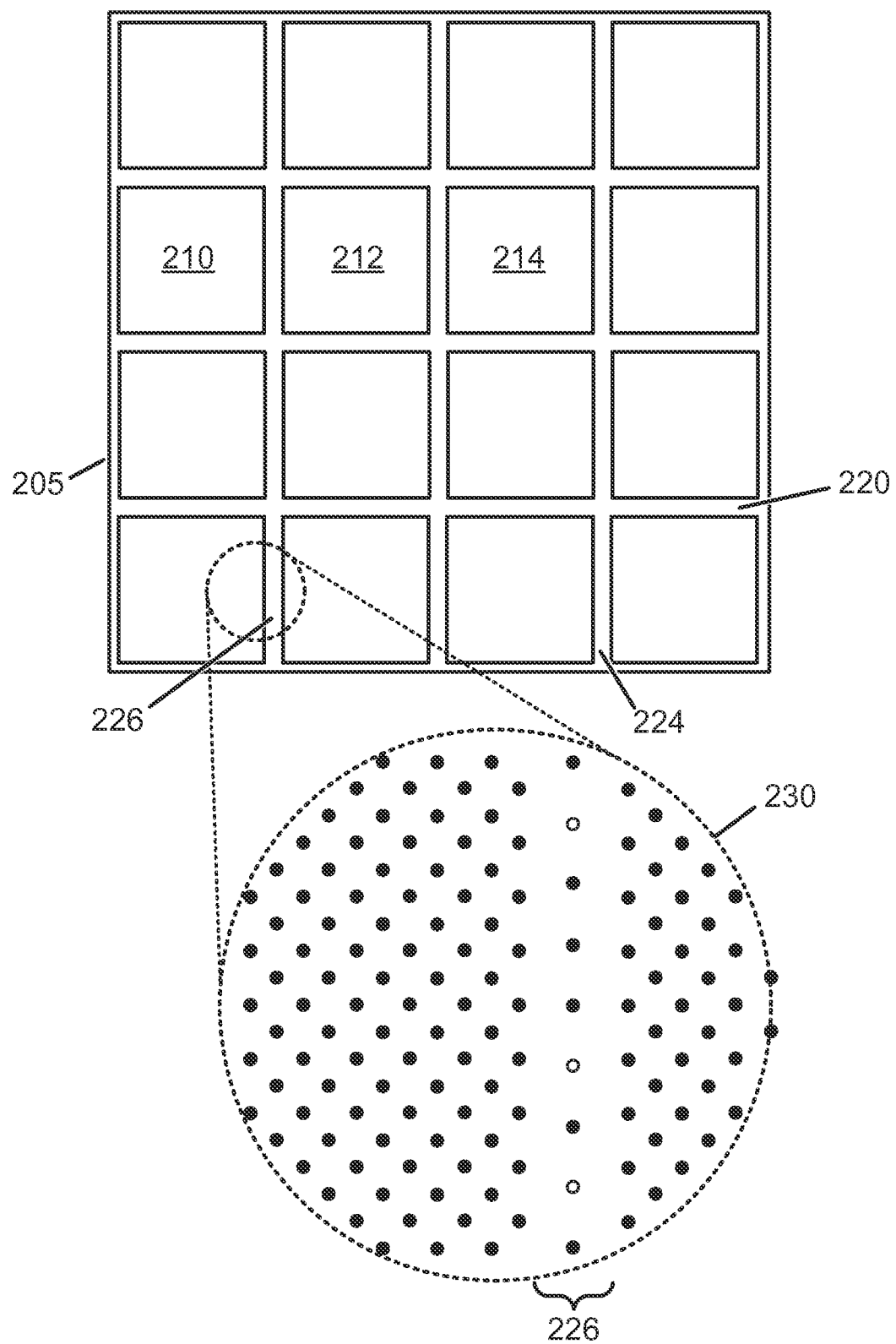
FIG. 2 is a top plan view with an inset of one field of an example high-density biochemical array chip showing details of a field region and one track region (size not to scale).

FIG. 2 is a diagram of one field 205 of a high-density biochemical array chip. The field is divided into subfields (e.g. 210, 212, 214) separated by track regions that are aligned substantially along a horizontal X dimension (e.g. track region 220) and by track regions that are aligned substantially perpendicular to the X dimension regions along a vertical Y dimension (e.g., track regions 224, 226). A magnified view 230 shows spots in two subfields separated by track region 226. The chips of FIGS. 1 and 2 do not include any marks or features used for alignment other than track regions that separate the subfields. Properties of the track regions, principles by which they are laid out, and their relationship to the subfields are discussed in detail below.

Figure 3:
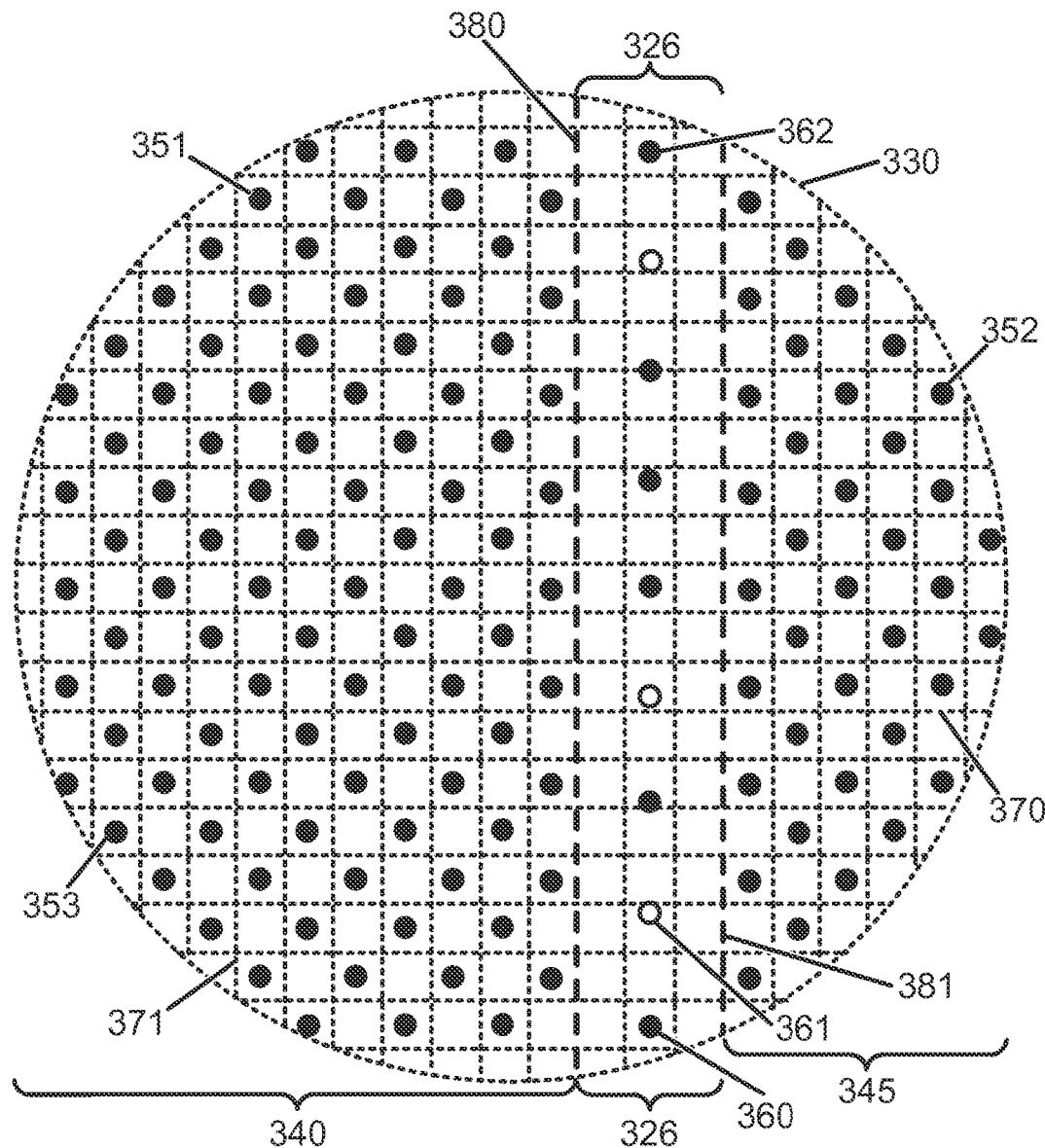
FIG. 3 is a top plan view of part of a subfield of one field region and one track region of an example high-density biochemical array chip illustrating one embodiment of a layout pattern of attachment sites relative to an overlay of pixels showing relative scale and position in accordance with the invention.

FIG. 3 is a diagram of part of a subfield of one field of a high-density biochemical array chip according to an example embodiment. The circular area 330 represents the same magnified view of a field as view 230 in FIG. 2. In this view, for illustration purposes only, track region 326 is bounded by heavy dashed lines 380 and 381; in practice however, such dashed lines are not present on the array chip itself.

In the embodiment illustrated in FIG. 3, the width of vertical track region 326 is set to equal the length of 3 object space pixels, which correspond to camera (or image space) pixels according to the applicable magnification. In this embodiment, the height of a horizontal track region may be the same as the width of track region 326. In some embodiments, the width of a vertical track region (and similarly, the height of a horizontal track region) may be equal to 5 object space pixels in the array grid of the adjacent non-track regions. As illustrated in FIG. 3, a site-free band separates track region 326 from each of the adjacent regions 340 and 345. In operation, these site-free bands prevent the light signals, emitted from the experiments disposed on the more densely populated regions 340 and 345, from interfering with the signals emitted from the experiments disposed on the sites of track region 326. In other embodiments, the track region does not need to be separated from the field regions with site-free bands; rather, in these embodiments a correlator logic may be used to correctly process the signals recorded in an image of the track region even if the track region is embedded into a field region without a separation site-free band. For example, the correlator logic may be configured to distinguish between the "on-pitch" signals from the field region and the different, "off-pitch" signals of the track region by relying on the property that "on-pitch" signals tend to get easily canceled out by averaging to zero.

In the embodiment of FIG. 3, regions 340 and 345 are parts of adjacent subfields on either side of track region 326. Fluorescent spots (e.g. 351, 352, and 353) appear in the subfields; fluorescent spots (e.g. 360, 362) are also seen in the track region 326. In this embodiment, there is no difference in the biochemical experiments disposed on subfield spots and track region spots, or in the fluorescent markers that are used to tag the experiments. Open circles (e.g. 361) represent the intentional absence of a spot, e.g., a deletion spot. Such deletion spots are conveniently made by deleting corresponding features on a photolithography mask used to pattern the sites on an array chip. According to the principles described herein, the deletion spots preferably account for more than 5% of the available spot locations in the track region but less than 15%. The spots in the track region may be attachment sites for biochemical or fluorescent molecules, the same or similar to sites in the field region. The deletion spots may be the absence of attachment sites, or they may be attachment sites that have been subsequently chemically treated to inhibit or prevent binding with biochemical or fluorescent molecules.

For illustration purposes only, light dashed lines (e.g. 370, 371) in FIG. 3 indicate the boundaries between the object space pixels that correspond to the boundaries of the physical pixels (e.g., the image space pixels) in a camera that is used to image the chip at a specific magnification. Thus, while FIG. 3 is drawn at a resolution much finer than a camera's pixel period, an image of region 330 taken with a camera having pixels bounded by the light dashed lines in the figure could not resolve spatial features finer than the pixel period. Despite this limitation, the layout of spots in the track region permits alignment of spots to pixels with sub-pixel resolution as described below.

The layout of spots on the chip shown in FIG. 3 (and therefore the layout of the biochemical experiments on the chip in operation) provides for a two-to-one ratio of object space pixels to array spots in regions 340 and 345 that are part of subfields on the array chip. That is, the area in regions 340 and 345 is configured at a density of two object space pixels per one array spot. To the extent that track regions take up only a few percent of the total area of a field, the two-to-one pixel to spot ratio holds approximately for an entire chip. Higher density layouts are possible, however, as further described below.

For example, FIG. 3 illustrates an array chip in which the spots in the subfield regions are disposed on an array in a checkerboard pattern. An array with a checkerboard pattern has a spot pitch of:

$$\sqrt{2} * \text{the array pitch},$$

and it is the diagonal distance between the centers of any two adjacent spots. For example, for an array with an object space pitch of 500 nm, the spot pitch defining a checkerboard pattern would be:

$$\sqrt{2} * 500 = 707 \text{ nm}.$$

Viewed in another way, in an array with spots arranged in a checkerboard pattern, the spots in each adjacent row are offset by ±1 column.

In fluorescent imaging, using a checkerboard pattern on an array chip helps because light from a chip spot may typically bleed horizontally or vertically across to adjacent spots but not to corner spots. Thus, disposing the spots of an array chip in a checkerboard pattern allows for the very high density of two object space pixels (and, therefore two camera pixels) per one spot while at the same time minimizing the crosstalk from signal bleeding within the electronics of the imaging instrument.

Figure 4:
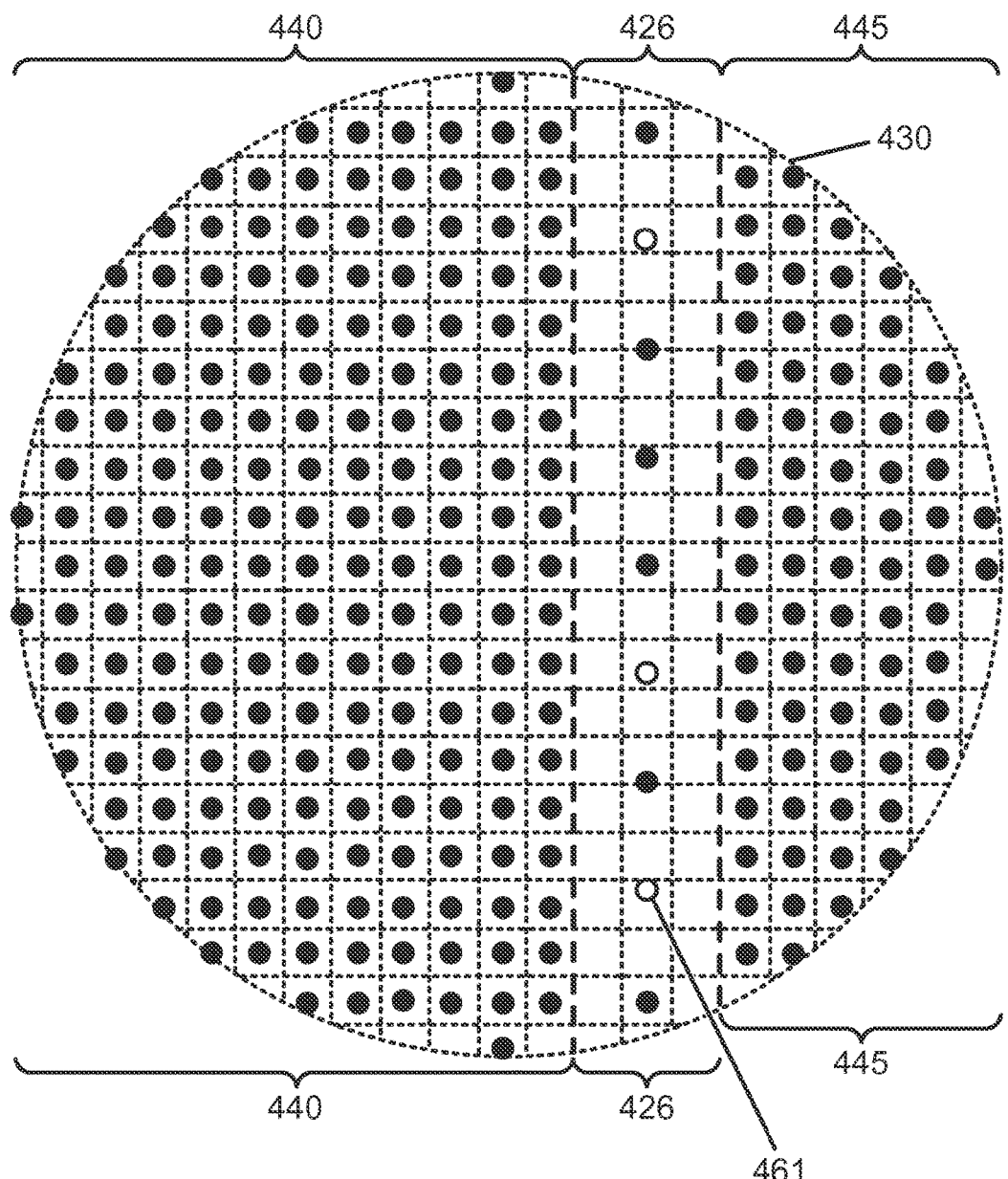
FIG. 4 is a top plan view of part of a subfield of one field region and one track region of an example high-density biochemical array chip illustrating another embodiment of a layout pattern of attachment sites relative to an overlay of object space pixels showing relative scale and position.

FIG. 4 is a diagram of part of a subfield of one field of a high-density biochemical array chip according to an example embodiment. FIG. 4 is similar to FIG. 3 except that in FIG. 4, the object space pixel (and, therefore, the camera pixel) to array spot ratio is one-to-one in the subfields. Circular area 430 represents the same magnified view of a field as view 230 in FIG. 2 and view 330 in FIG. 3. In this view, for illustration purposes only, track region 426 is bounded by heavy dashed lines; in practice however, such dashed lines are not present on the array chip itself.

In the embodiment illustrated in FIG. 4, the width of vertical track region 426 is set to equal the length of 3 array (or object space) pixels, which correspond to camera (or image space) pixels according to the applied magnification. In this embodiment, the height of a horizontal track region on the array chip may be the same as the width of track region 426. In other embodiments, the width of a vertical track region (and similarly, the height of a horizontal track region) may be equal to 5 object space pixels in the array grid of the adjacent non-track regions. As illustrated in FIG. 4, a site-free band separates track region 426 from each of the adjacent regions 440 and 445. In operation, these site-free bands prevent the light signals, emitted from the experiments disposed on the more densely populated regions 440 and 445, from interfering with the signals emitted from the experiments disposed on the sites of track region 326. In other embodiments, the track region does not need to be separated from the field regions with site-free bands; rather, in these embodiments a correlator logic may be used to correctly process the signals recorded in an image of the track region even if the track region is embedded into a field region without a separation site-free band. For example, the correlator logic may be configured to distinguish between the "on-pitch" signals from the field region and the different, "off-pitch" signals of the track region by relying on the property that "on-pitch" signals tend to get easily canceled out by averaging to zero.

Regions 440 and 445 are parts of adjacent subfields on either side of track region 426. Fluorescent spots (shown as black dots) appear in the subfields and in the track region. There is no difference in the biochemical experiments represented by subfield spots and track spots, or the fluorescent markers used to see them. Open circles (e.g. 461) represent the intentional absence of a spot (e.g., a deletion spot). Such deletion spots may be conveniently made by deleting corresponding features on a photolithography mask used to pattern the sites on an array chip.

The layout of spots shown in FIG. 4 (and therefore the layout of the biochemical experiments on the chip in operation) provides for a one-to-one ratio of object space pixels to array spots in regions 440 and 445 that are part of subfields on the array chip. That is, the area in regions 440 and 445 is configured at a density of one object space pixel (and, therefore, one camera pixel) per one array spot. This layout leads to a very large amount of information contained in each field image. For example, in the embodiment illustrated in FIG. 4, approximately 5% of the chip area is used for track regions and the remaining 95% percent of the chip area is used at maximum density of one object space pixel (and, therefore, one camera pixel) per one array spot.

In other embodiments according to the principles described herein, the sites in the non-track regions of an array chip may be disposed in a layout that provides a density of 4 object space pixels (and, therefore, 4 camera pixels) per one site. Even though such 4:1 pixels-per-site density is lower than the site densities illustrated in FIG. 3 and FIG. 4, it is still a very high density when compared with the densities of conventional array chips; at the time of filing of the present application, commercially available biochemical array chips have densities in the range of 10:1 to 25:1 pixels-per-site density.

The design of the high-density array chips described herein leaves little room for imaging error because misalignment of camera pixels and array spots of as little as one quarter (0.25) pixel period can lead to unacceptable data acquisition errors. To address this, described below are techniques for designing array chips with track regions that provide for alignment within a desired tolerance, as well as techniques for using Moiré averaging in correcting alignment errors.

Determination of the Parameters for the Track Region Structure

According to the principles and embodiments described herein, the layout of the sites in a track region (also referred to as "track sites") is determined in accordance with the desired tolerance for aligning the camera pixels with the sites on the array chip. To determine how many track sites are necessary to achieve a particular sub-pixel alignment tolerance (and therefore the pitch of the track region), the following calculations may be used.

As an example, suppose that an alignment tolerance measurement error of 5 nm is desired for a perfectly pre-aligned system and Moiré averaging is to be used for aligning the camera pixels with the sites on an array chip. The measurement error of any site in the track to the array may be as large as ±0.5 pixels, and thus the averaged error for an individual object space pixel i is approximately 0.25 pixels, e.g., $|[(error)]_\perp i| \approx 0.25 *$ the size of an object space pixels.

For the purposes of Moiré averaging, the averaged alignment error is the difference between the average of the sum of all alignment errors and the correct alignment value, that is $$\frac{1}{N} \sum_{i=1}^{N} error_i - correct_{value} \approx \qquad (1)$$

$$\frac{1}{4} * \frac{1}{\sqrt{N}} * \text{the size of an object space pixel}$$

where N is the number of measurements (e.g., number of track sites emitting signals) and "correct_value" is the actual (but unknown) alignment error. For example, if the desired accuracy is $\frac{1}{40}^{th}$ of an object space pixel, then the desired N is about 100.

In an array chip with 8 track regions each having 8 sub-regions that each has 59 track sites, there are a total of

8*8*59=3776 track sites. Since in DNA sequencing a target nucleic acid will generate a signal a quarter of the time on average (e.g., a target nucleic acid will produce a signal for either A, T, C, or G), only about quarter of the track sites can be expected to emit a signal. That is, it can be expected that approximately 944 sites (e.g., 3776/4) will emit a signal during operation. According to equation (1) above, with N=944 the theoretical averaged alignment error can be expressed as $$\frac{1}{4} * \frac{1}{\sqrt{944}} * \text{the size of an object space pixel.}$$

Thus, for an object space pixel of 500 nm, the theoretical averaged alignment error is $$\frac{1}{4} * \frac{1}{\sqrt{944}} * 500 \approx 4.07 \text{ nm.}$$

Practical observations for array chips with 500 nm object space pixels have confirmed that the practical measured error for 59 track sites per track sub-region is about 5 nm, which is close to the theoretical value.

The above calculations indicate that a certain number of track sites arranged in a track region along a single dimension (e.g., such as a horizontal X dimension or a vertical Y dimension) allow for using Moiré averaging to calculate the X-Y alignment errors and to align the camera pixels with the array chip sites to within a desired tolerance. (It is noted that in one embodiment, a tolerance of 5 nm is sufficient for taking accurate signal intensity measurements in DNA sequencing.) In addition, the above calculations indicate that a very low alignment tolerance (e.g., such as 5 nm) can be achieved by losing only about 5% of the array chip area to track regions, which is very useful in implementations (such as high throughout DNA sequencing) where high density of array spots is necessary for efficient operation.

Alignment Correction by Using Moiré Averaging

The track regions of the high-density array chips described herein (e.g., as illustrated in FIG. 3 and FIG. 4) are designed such that an imaging system can use them for several simultaneous operations: (1) alignment of fields with sub-pixel precision; and (2) absolute location of spots in a pixel coordinate system. Principles underlying the first of these operations, alignment of fields with sub-pixel precision, are discussed in connection with FIGS. 5 and 6.

Figure 5:
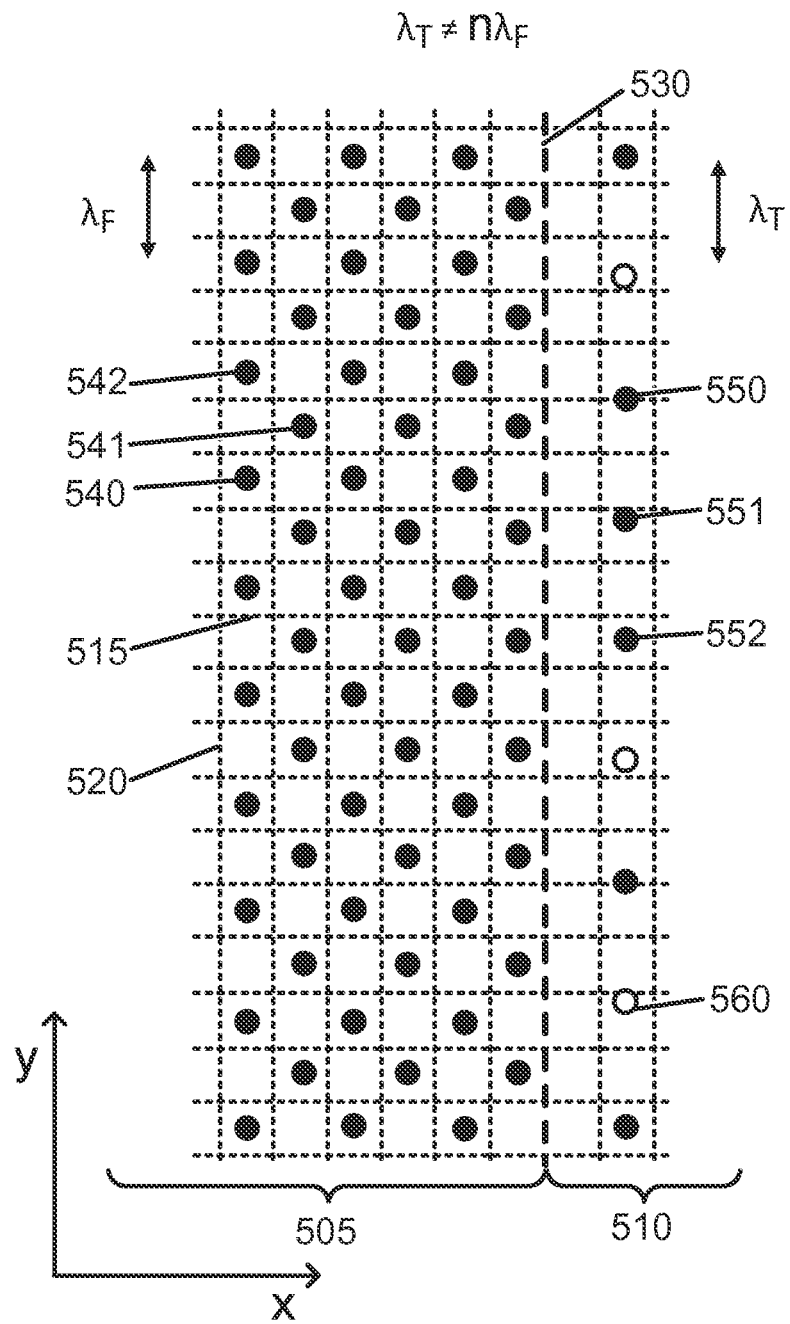
FIG. 5 is detail of a portion of FIG. 4 for illustrating that the period of the field region and the track region are non-integer multiples of one another.

FIG. 5 is a diagram illustrating relationships between periods of subfield spots and alignment track spots in a high-density biochemical array chip. FIG. 5 shows a small section of a subfield 505 and an adjacent track 510 in a field of a chip having a two-to-one camera pixel to array spot ratio in which the spots are arranged in a checkerboard pattern. (The entire discussion of FIG. 5 would be unchanged, however, if the pixel to spot ratio were one-to-one.) Light dashed lines (e.g. 515, 520) show the boundaries between object space pixels that correspond to the boundaries of the physical pixels (e.g., the image space pixels) in a camera that is used to image the chip at a specific magnification, while heavy dashed line 530 marks the boundary between subfield region 505 and track region 510. (It is noted that the light dashed lines 515, 520 and the heavy dashed lines 530 are included in FIG. 5 for illustration purposes only; in practice, such dashed lines are not present on the array chip itself.)

Field spots (e.g. 540, 541, and 542) in subfield 505 are repeated in the X and Y dimensions with a period $\lambda_F$, where $\lambda_F$ is the period for field spots. Track spots (e.g. 550, 551, and 552) in track region 510 are repeated in the Y dimension with a period $\lambda_T$, where $\lambda_T$ is the period for spots in the track region. (Deleted spots, drawn as open circles (e.g. 560), are included when measuring the track spot repetition period.) By the design of the array chip, there is an intentional, non-integer-multiple mismatch between $\lambda_F$ and $\lambda_T$; i.e. $\lambda_T \neq n \lambda_F$ where n is an integer. The mismatch may be easily seen in FIG. 5 as some track spots lie near the middle of an object space pixel (e.g. track spot 552) while others lie near pixel boundaries (e.g. track spot 550).

When the period of field spots is the same as, or an integer multiple of, the object space pixel period that corresponds (under the applied magnification) to the pixel period in a camera used to image a chip, the careful choice of a non-integer-multiple ratio between the period of field spots and the period of track spots increases the ability to accurately align a camera with the spots on the chip during operation. The increased accuracy is obtained because the diversity of track spot locations within the object space pixels may be averaged to calculate an average track spot position. If the track spots' period were the same as that of the camera pixels, errors of as much as $$\frac{\lambda_P}{\sqrt{2}}$$

(where $\lambda_P$, the object space pixel period, is equal to or an integer sub-multiple of $\lambda_F$) could result. This one-dimensional Moiré averaging alignment technique is illustrated in FIG. 6.

Figure 6:
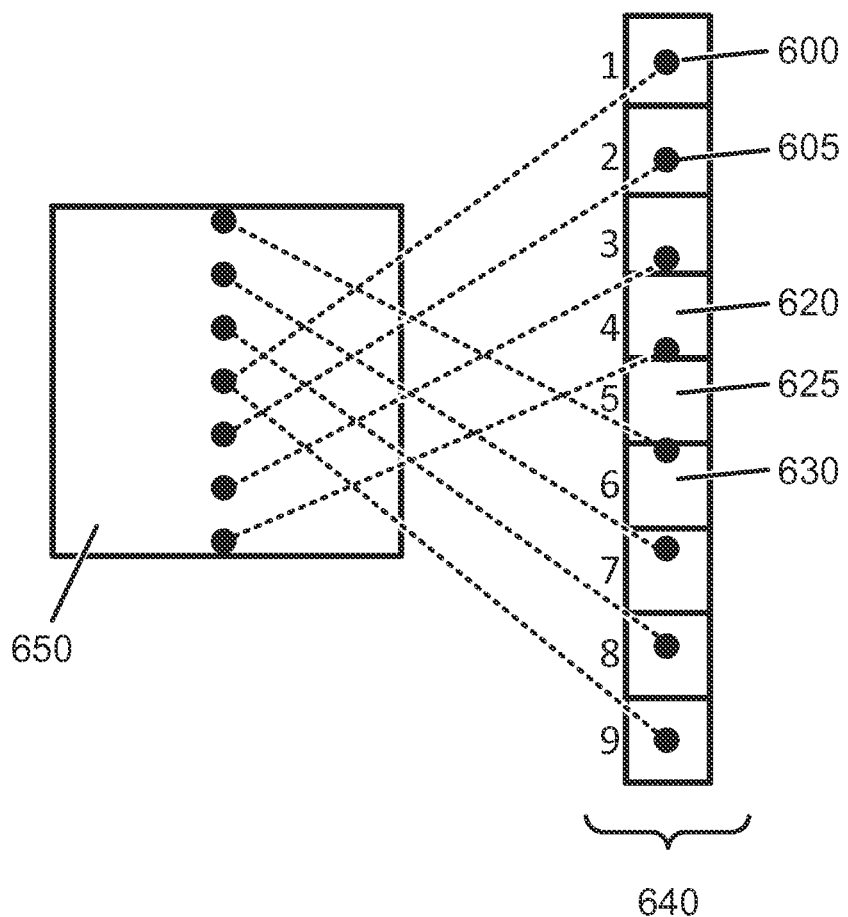
FIG. 6 is a diagram for illustrating one-dimensional "Moiré averaging" techniques.

A track spot period, $\lambda_T$, that is not an integer multiple of the object space pixel period, $\lambda_P$, is shown in a conceptual, one-dimensional example of imaging track spots in FIG. 6. In FIG. 6, a line of track spots including spots 600, 605, etc., has a period or pitch between spots, of $\lambda_T$. A line of object space pixels (which, subject to the applied magnification, correspond 1:1 with camera pixels), including pixels 620, 625, 630, etc., has a period of $\lambda_P$. For illustration purposes, in the example of FIG. 6, $8\lambda_T=9\lambda_P$ (equivalently, $\lambda_T=1.125\lambda_P$). When the track spots are observed with the line of pixels (as shown at 640 where the pixels are labeled "1" through "9"), the track spot and object pixel are aligned every ninth pixel. The relative positions of the track spots and pixels sweep through each other in the intervening pixels. Inset 650 is a magnified view of object space pixels "1" through "9" superposed upon each other. The track spots are spread evenly across the superposed pixel. The difference in track spot pitch and pixel period leads to the track spots sampling the length of the pixel in equal steps. The average of all the track spot locations in superposition 650 leads to an estimate of the best fit track spot location in pixel coordinates with an error that is reduced by a factor of $$\frac{1}{\sqrt{N}}$$

where N is the number of pixels between repeats; N=9 in this example. In practice, in one embodiment an array chip is configured with N=59 track spots that are evenly spread over 125 object space pixels, thereby yielding a track spot pitch of $$\lambda_T = \frac{125}{59}\lambda_P,$$

or $\lambda_T$=2.1194. In another embodiment, an array chip is configured with N=67 track spots that are evenly spread over 125 object space pixels, thereby yielding a track spot pitch of $$\lambda_T = \frac{125}{67}\lambda_P,$$

or $\lambda_T$=1.8664.

Thus, the location of the track spots may be determined with sub-pixel precision using Moiré averaging, as described below.

The operation for determining the absolute location of spots in a pixel coordinate system can be performed based on the information encoded in the layout of spots in the track region as follows. If the position of the track spots is known, the position of field spots may be calculated based on the known layout of subfield and track spots on a chip. The position of track spots may still be subject to offset errors of integer numbers of track spot periods, however. That is, during operation the camera pixels may be aligned with the object space pixels with sub-pixel precision, as described above, but there may still be misalignment by one or more pixels such that a particular camera pixel is aligned with the wrong object space pixel. Such "modulo one" track spot pitch ambiguities may be resolved through the use of deleted track spots, such as deleted spot 560 in FIG. 5.

Figure 7:
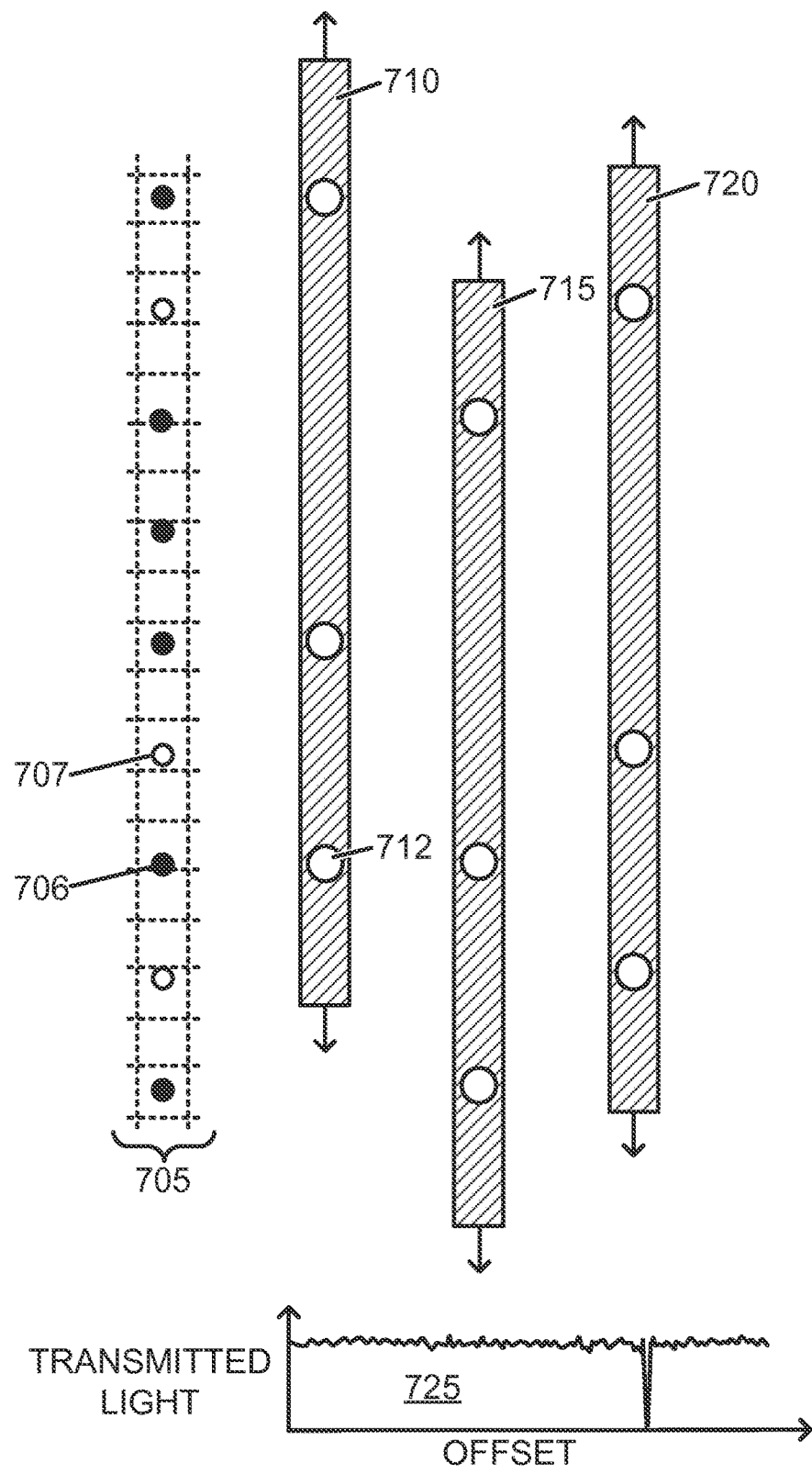
FIG. 7 is a diagram for illustrating offset determination using deletion patterns.

The absolute location of track spots (and therefore field spots that are fixed relative to the track spots when the array chip is manufactured) may be determined by analysis of track spot deletion patterns as illustrated in FIG. 7. In FIG. 7, track 705 has both regular illuminated spots (e.g. 706) and deleted spots (e.g. 707), corresponding to active and deleted attachment sites, respectively, on a chip. For illustration purposes, masks 710, 715 and 720 are shown as aids to conceptualization of cross correlating a known deletion pattern with an image of track spots. Masks 710 and 715 are misaligned (by plus or minus one spot) while mask 720 is aligned with the deletion pattern. When misaligned mask 710 or 715 is superposed with track 705, light is transmitted through transparent openings such as 712. On the other hand, when mask 720 (which is correctly aligned with the deletion pattern of track 705) is superposed with track 705, very little light passes through its transparent openings as they line up with deleted spot locations. Graph 725 shows transmitted light versus offset during cross correlation of a mask pattern with an image of a track encoded with a deletion pattern. The intensity of transmitted light drops sharply when the mask and track are at the proper offset with respect to one another. This correlation property of masks with deleted spots is used in practice by a correlation logic that is configured to take as input an ordered data set representing the intensities recorded from the track spots and an ordered data set representing the mask of deleted spots (which is known and fixed relative to the object-space pixel coordinate system), and to generate as output an alignment error term that specifies the offset of the track spots (in whole pixels) from their correct location in the pixel coordinate system.

If the deletion pattern for a track region is pseudo random, then the pattern has a wide spatial range; e.g., only one peak will appear in a cross correlation of the pattern and an image of the track region. If the deletion pattern is periodic, or partly so, more than one peak may appear in a cross correlation. Thus, pseudo-random deletion patterns are robust when the position of a track region must be identified with no a priori information. On the other hand, initial rough alignment may be good enough that deletion patterns are not required to be strictly pseudo random.

Example Method of Using Moiré Averaging for Alignment Correction

In operation, when target nucleic acids are disposed on an array chip, Moiré averaging can be used to calculate the correction alignment term and to apply this term during the process of initial chip registration (e.g., when the chip is affixed in a sequencing machine stage prior to imaging) and during the process of continuously taking images of the chip (e.g., in a feed control that continuously corrects the alignment of the imaging instrument during imaging). The correction alignment term, $E_T$ for a single dimension (such as an X dimension or a Y dimension), is expressed as follows $$E_T = \lambda_T * e_d + e_{sp} \quad (2)$$

where $E_T$ is the correction alignment term for the specific single dimension, $\lambda_T$ is the pitch of sites in the track region along the single dimension, $e_d$ is the track pitch (whole-pixel) misalignment error that is an integer value indicating whole pixels, and $e_{sp}$ is the sub-pixel error determined by using Moiré averaging. The size of the sub-pixel error, $e_{sp}$, is less than the size (length or width) of an object space pixel as expressed by the following inequality:

$$-\frac{\lambda_T}{2} < e_{sp} < \frac{\lambda_T}{2}$$

where $\lambda_T$ is the pitch of sites in the track region along a single dimension (e.g., the X dimension or the Y dimension). Since in practice correction alignment may be needed both in the X dimension and the Y dimension, a first correction alignment term is computed for the X dimension based on information from a horizontal track region on the chip, and a second correction alignment term is computed for the Y dimension based on information from a vertical track region on the chip. The two correction alignment terms are then both applied in order to achieve the desired alignment between the camera pixels and the spots on the array chip.

In an example embodiment, a method for aligning an array chip comprises several steps. In the first step, an image of the sites in a track region (on which target nucleic acids have been disposed) is taken, and the signal intensities recorded in the image are converted into an ordered data set. For example, the camera in an imaging instrument may snap one or more images of a track region disposed along a single dimension, and an image processing logic may generate an ordered data set (referred to herein as "track site data set") that represents (e.g., as a linear profile) the intensities and positions of signals emitted from the track sites.

In the next step, the track site data set is correlated to an ordered data set (referred to herein as "expected data set") representing (e.g., as a linear profile) the known/expected positions of track sites that are defined by the site pitch of the track region. Using Moiré averaging, the correlation returns the sub-pixel error for the particular dimension along which the track region is disposed. For example, a correlation logic may obtain the sub-pixel error based on multiplying the track site data set and the expected data set. In another example, correlation logic takes as input the track site data set and the expected data set, and then associates (discretizes) each signal recorded in the track site data set to one discrete member of the track site data set. To perform Moiré averaging, the correlation logic shifts the expected data set with respect to the track site data set by ±1 track pitch (~2 pixels) object space pixels in sub-pixel increments. For each shift, the correlation logic computes: (a) the $\chi^2$ error for each member of the track site data set representing a recorded signal based on the distance of that member to the closest member in the expected data set that represents an expected track site; and (b) the sum of the squares of all the $\chi^2$ errors computed for that shift. The correlation logic then determines the sub-pixel error based on the smallest computed squared-error sum from all shifts. This type of Moiré averaging determines the sub-pixel error for the entire track region along the single dimension and, therefore, also determines the sub-pixel error for the field regions of the chip, which are fixed relative to the track region when the chip is manufactured. The Moiré averaging mechanism effectively averages the error terms, error$_i$, of all track sites that have emitted a signal without actually knowing or determining the exact offset of each individual track site from the center of some object space pixel. The operations in this step may be performed separately for the X dimension (on a track site data set representing a track region in the horizontal X dimension) and for the Y dimension (on a track site data set representing a track region in the vertical Y dimension) to determine the sub-pixel error for the X dimension and the sub-pixel error for the Y dimension, respectively.

In the next step, the track site data set is correlated to ordered data sets representing (e.g., as linear profiles) one or more patterns of deletion spots in the track regions (referred herein as the deletion data sets). The correlation returns the track pitch misalignment error for the particular dimension along which the track region is disposed. For example, a correlation logic may take as input the track site data set and the deletion data sets. The correlation logic then compares the track site data set and the deletion data sets to determine that one deletion data set which most closely matches to the track site data set. The correlation logic then computes the track pitch misalignment error as the offset, in whole pixels, between the track site data set and the matching deletion data set. The operations in this step may be performed separately for the X dimension (on a track site data set representing a track region in the horizontal X dimension) and for the Y dimension (on a track site data set representing a track region in the vertical Y dimension) to determine the track pitch alignment error for the X dimension and the track pitch alignment error for the Y dimension, respectively.

In the next step, equation (2) above is used to determine the correction alignment term for the dimension along which the track region is disposed based on the pitch of the sites in the track region (which is known), the sub-pixel error computed for the track region, and the track pitch alignment error computed for the track region. For example, a correction logic may use equation (2) and the computed sub-pixel error and track pitch alignment error to calculate the correction alignment term for the track region. The operations in this step may be performed separately for the X dimension (for a track region along the horizontal X dimension) and for the Y dimension (for a track region along the vertical Y dimension) to determine correction alignment term for the X dimension and the correction alignment term for the Y dimension, respectively.

In the final step, the camera pixels and the array grid of the array chip may be aligned by the amount of the correction alignment terms for the X dimension and the Y dimension. For example, a lateral offset system in the imaging instrument may adjust a galvo to shift the position of images in the camera based on the correction alignment term for the X dimension. A time-delay integration (TDI) offset system in the imaging instrument may adjust the pulse timing of the camera based on the correction alignment term for the Y dimension. In this manner, the camera pixels and the array grid of the chip may be aligned with each other within the tolerance for which the layout of the track regions in the chip has been designed as described heretofore.

The principles of designing the layout of track sites and the Moiré averaging-based alignment described herein may be used in various methods at various stages in the examination of biochemical experiments disposed on an array chip. For example, in some embodiments, the Moiré averaging alignment based on track region information as described herein may be used to align an array chip during the process of initial chip registration when the chip is affixed in a sequencing machine stage prior to imaging.

In other embodiments, the Moiré averaging alignment based on track region information as described herein may be used in a feed-forward control loop during the process of continuously taking images of the chip, where the alignment of the imaging instrument is corrected after taking each scan of the chip. For example, since scanning two adjacent columns of a chip results in negligible error offsets (e.g., 10-20 nm or less), the X and Y correction alignment terms can be accumulated across scans without losing significant alignment accuracy. Thus, after scanning a column and calculating its X and Y correction alignment terms, a feed-forward logic may add these two terms to the corresponding correction alignment terms that have been accumulated for the previously-scanned columns. In this manner, the correction alignment terms for the X and Y dimensions for a currently scanned chip column are used to adjust the imaging instrument before the next chip column is scanned, thereby achieving a feed-forward alignment.

In summary, the layout of a high-density biochemical array chip affects the rate of biochemical experimental data that may be extracted from the chip. A high density of experiments may be achieved by matching the imaged repetition period of experiments to the pixel period (or a small integer multiple of the pixel period) of a camera. Data acquisition speed depends on alignment, absolute location, and identification of features in experimental images obtained, for example, by fluorescence microscopy. A chip layout with asynchronous tracks enables alignment within a desired tolerance. Moiré averaging may be used with asynchronous tracks to determine sub-pixel alignment, while track deletion patterns facilitate resolution of modulo one errors that may be used for precise track pitch alignment. For the purposes of Moiré averaging, the correction alignment terms in the X and Y dimensions are obtained from information reflecting a deliberately misalignment, during manufacture, between the sites in a track region with the grid on which the sites in a regular field region lie. A prime number (e.g., such as 59 or 67) is used to define such deliberate misalignment determine the alignment in order to achieve the necessary accuracy within a desired tolerance.

In an operational context of DNA sequencing, an example embodiment of an array chip with track regions as described herein allows a sequencing machine to extract the location of a snapped image with respect to the array chip at least as fast as the machine is taking the images. For example, in a sequencing machine comprising two cameras that are taking images of an array chip at a rate of 30 frames per second (fps) each, 1000 images come through the machine every 15 seconds. By using array chips with track regions as described herein, the sequencing machine (or a component thereof) can determine the X-Y location of each image with respect to the chip within 15 milliseconds or less. Specifically, by using array chips with track regions as described herein, in one implementation a sequencing machine was able to determine the X-Y location of images at a rate of 10 milliseconds with an accuracy of 5 nm.

Array Chip Construction

In some embodiments, array chips are constructed by disposing one or more layers (e.g., such as a reflective layer and/or a fluorescence enhancement layer) on a substrate. For example, the substrate of an array chip may itself be composed of a reflective material (e.g., such as a metal or a Bragg reflector), or it may be a base of substantially any coatable material that provides a solid support on which a fluorescent reflective layer can be disposed. The fluorescent reflective layer of the substrate may be made up of a thin, transparent, dielectric layer or a stack of thin, transparent, dielectric layers, where such dielectric materials include, but are not limited to, $SiO_2$, $TiO_2$, $Ta_2O_5$, $HfO_2$, $ZrO_2$, MgO, $Si_3N_4$, $MgF_2$ and $YF_3$.

In some embodiments, the sites on an array chip (e.g., such as sites in track regions and sites in field regions) may be defined by depressions or raised areas in the fluorescence reflective layer of the chip substrate. In such embodiments, the array chip sites may be between 30-1000 nm in width and/or length, and in a preferred aspect the sites may be 200-500 nm in width and/or length, even more preferably approximately 300 nm in width and/or length. In another specific aspect, the array chip sites may be separated by a distance of between 0.2 µm and 10 µm. Target nucleic acids (e.g., such as nucleic acid macromolecules) can be placed on the array chip sites to form an assay. The target nucleic acids are ideally disposed within each discrete site in a manner that provides very high density and discrete analysis of the individual nucleic acid constructs contained therein. In specific aspects, each site of an array chip is configured to accept a single macromolecule and, when macromolecules are disposed on the chip, a single macromolecule attaches in each site. In some embodiments the distance between the target nucleic acid molecules, which have attached to the sites on an array chip, provides discrete analysis (e.g., such as sequence determination) for at least 30% of the nucleic acid constructs, preferably at least 50% of the nucleic acid constructs, more preferably at least 70% of the nucleic acid constructs, and even more preferably at least 90% of the nucleic acid constructs in the target nucleic acid molecules.

The substrate layer(s) of the array chips described herein can be constructed using various multi-layer coating technologies. The optimization of the multilayer coating design can be done by applying one or more now-known or later-developed techniques. For example, a substrate base may be coated by any one of the following methods: thermal and/or electron beam vapor deposition, replication, transfer, film deposition, by processes of the CVD type (e.g., like LPCVD, PECVD etc.) or of the PVD type such as sputtering (e.g., like DC magnetron sputtering). Ion-assisted deposition processes can be used as well as the sol-gel process. Substrate layers may be optionally transferred onto the substrate base by bonding or molecular adhesion.

In embodiments where depressions or raised areas in a fluorescence layer of an array chip substrate are desirable, multi-layer deposition on a reflective substrate base (or on a reflective layer thereof) may be used to produce the desired structures. For example, a multilayer dielectric fluorescence layer can be designed using a layer of a material with a higher refractive index e.g., $Si_3N_4$ (having a refractive index of n=2.0), disposed on a dielectric material with a lower optical refractive index such as $SiO_2$ (n=1.48). Other coating materials, including multilayer coatings comprising more than two materials, can be used as well. In some embodiments, various structures may be constructed in the fluorescence layer in order to improve the detection of the fluorescence signals emitted from the material dispensed thereon; examples of such enhancement structures are described in U.S. patent application Ser. No. 12/261,447 filed on Oct. 30, 2008, the entire content of which is hereby incorporated by reference is fully set forth herein.

Etching can be provided by multiple available techniques, such as the damascene technique, whereby openings are selectively etched into a dielectric layer. Generally, a photoresist material is layered onto the dielectric layer and a pattern of openings is outlined in the photoresist layer using lithographic techniques. An anisotropic etch is then used to form the openings in the dielectric layer. The photoresist material is then removed. Where multiple layers and depths are desired, such a process requires the use of more than one mask layer with varying resistances to the anisotropic etch processes.

Use of Array Chips with Track Regions in Biochemical Assays

The principles and embodiments described herein provide for improved array chips that may be used as part of an overall system for biological assays. In preferred aspects, the array chips described herein may be used for polynucleotide analysis including, but not limited to, expression and transcriptome analysis using nucleic acid microarrays, PCR and other polynucleotide amplification reactions, SNP analysis, proteome analysis, and the like, and particularly nucleic acid sequence determination. The following patent applications provide additional information on various assays that may be used in conjunction with the array chips described herein: U.S. patent application Ser. No. 11/451,691 filed on Jun. 13, 2006, Ser. No. 11/679,124 filed on Feb. 24, 2007, Ser. No. 12/325,922 filed on Dec. 1, 2008, and in various systems such as those described in U.S. patent application Ser. No. 12/261,548 filed on Oct. 30, 2008; the entire contents of the applications referred to in this paragraph are hereby incorporated by reference as if fully set forth herein.

In some embodiments, the array chips described herein may be adapted so as to be suitable for use in performing replication and/or amplification (e.g., circle dependent replication, circle dependent amplification, or polymerase chain reaction amplification) on samples attached to chips' substrates, e.g. by using capture oligos.

In certain embodiments, for example those envisaged for use with PCR or other reactions in which tightly controlled temperature regulation is required, the array chips described herein may be equipped with temperature control means to allow for rapid heating and cooling of the sample and PCR mix (e.g., thermal cycling). Typically, an array chip will be provided with an electrical heating element or a Peltier device. An array chip may also be adapted (e.g., by provision of cooling means) to provide for improved air cooling. Temperature control in the range 3°-105° C. is sufficient for most applications.

Sequence Determination

The array chips with track regions described herein may be used for a variety of biochemical analyses. One example of such analysis is sequence determination of target nucleic acids of unknown sequence. In various embodiments, a variety of sequencing methodologies may be used to determine a sequence of the target nucleic acid macromolecules using the array chips described herein, including but not limited to hybridization methods as disclosed in U.S. Pat. Nos. 6,864,052; 6,309,824; and 6,401,267; sequencing-by-synthesis methods as disclosed in U.S. Pat. Nos. 6,210,891; 6,828,100, 6,833,246; 6,911,345; Margulies, et al. (2005), Nature 437:376-380 and Ronaghi, et al. (1996), Anal. Biochem. 242:84-89; and ligation-based methods as disclosed in U.S. Pat. No. 6,306,597; Shendure et al. (2005) Science 309:1728-1739; to which reference is made for their teachings.

In some embodiments, the array chips described herein may be used for DNA sequencing of complete human genomes. Commercial viability of human genome sequencing services depends in part on the ability to sequence DNA rapidly and accurately. Thus, biochemical array chips can be used for DNA sequencing, can support large numbers of parallel DNA experiments, and can facilitate rapid and accurate genomic data acquisition. In DNA sequencing, biochemical experiments are performed on array chips by washing reagents over them according to precise protocols that specify chemical compounds and mixtures to be used, concentration, temperature, incubation time, and other parameters appropriate to a particular type of experiment.

One example of DNA sequencing of human genomes is the high-accuracy, combinatorial probe-anchor ligation (cPAL) sequencing that is commercially developed by Complete Genomics, Inc. of Mountain View, Calif. The cPAL sequencing technique relies on independently assaying each base from self-assembling DNA nanoballs (also referred to herein as "DNBs") that are loaded into patterned array chips. The first step in cPAL sequencing is loading a biochemical array chip with a random assortment of DNBs. A DNB is a macromolecule concatemer that contains multiple copies, linked in a series, of the same sequence of adapters and DNA fragments; the production of such concatemers is described, for example, in U.S. patent application Ser. No. 11/451,691, which was filed on Jun. 13, 2006 by Radoje Drmanac et al., the entire content of which is hereby incorporated by reference is fully set forth herein. A set of DNBs contains DNA fragments that can collectively span an entire human genome, but when the DNBs are first attached to the sites on an array chip (including sites in track regions and sites in field regions) there is no control over where any particular DNB goes. On the other hand, once the DNBs have attached to the chip sites, they stay there for all subsequent liquid processing steps and don't move from one site to another. In subsequent processing steps various reagents and buffers are washed over the DNBs on the array chip, and fluorescent signals from the DNBs are recorded with a fluorescence imaging instrument.

More specifically, the cPAL sequencing technique comprises cycling of the following steps. First, an anchor is hybridized to a first adaptor in the DNBs (typically immediately at the 5' or 3' end of one of the adaptors). Enzymatic ligation reactions are then performed with the anchor to a fully degenerate probe population of, e.g., 8-mer probes that are labeled, e.g., with fluorescent dyes. Probes may have a length, e.g., about 6-20 bases, or, preferably, about 7-12 bases. At any given cycle, the population of 8-mer probes that is used is structured such that the identity of one or more of its positions is correlated with the identity of the fluorophore attached to that 8-mer probe. For example, when 7-mer sequencing probes are employed, a set of fluorophore-labeled probes for identifying a base immediately adjacent to an interspersed adaptor may have the following structure: 3'-F1-NNNNNNAp, 3'-F2-NNNNNNGp, 3'-F3-NNNNNNCp, and 3'-F4-NNNNNNTp (where "p" is a phosphate available for ligation). In yet another example, a set of fluorophore-labeled 7-mer probes for identifying a base three bases into a target nucleic acid from an interspersed adaptor may have the following structure: 3'-F1-NNN-NANNp, 3'-F2-NNNNGNNp, 3'-F3-NNNNCNNp, and 3'-F4-NNNNTNNp. To the extent that the ligase discriminates for complementarity at that queried position, the fluorescent signal provides the identity of that base.

After performing the ligation and four-color imaging, the anchor 8-mer probe complexes are stripped and a new cycle is begun. With T4 DNA ligase, accurate sequence information can be obtained as far as six bases or more from the ligation junction, allowing access to at least 12 base-pairs (bp) per adaptor (six bases from both the 5' and 3' ends), for a total of 48 bp per 4-adaptor DNB, 60 bp per 5-adaptor DNB and so on.

Depending on which position a given cycle is aiming to interrogate, the 8-mer probes are structured differently. Specifically, a single position within each 8-mer probe is correlated with the identity of the fluorophore with which it is labeled. Additionally, the fluorophore molecule is attached to the opposite end of the 8-mer probe relative to the end targeted to the ligation junction. For example, an anchor may be hybridized such that its 3' end is adjacent to the target nucleic acid. To query a position five bases into the target nucleic acid, a population of degenerate 8-mer probes may be used, where the probes correlate with the fifth nucleic acid from the 5' end of the 8-mer probe, which is the end of the 8-mer probe that will ligate to the anchor. The 8-mer probes are individually labeled with one of four fluorophores, where a fluorophore of Cy5 is correlated with A, Cy3 is correlated with G, Texas Red is correlated with C, and FITC is correlated with T. (While this example describes use of four fluorophores to query a single base per cycle, it should be recognized that eight or sixteen fluorophores or more may be used per cycle, increasing the number of bases that can be identified during any one cycle.)

Many different variations of cPAL or other sequencing-by-ligation approaches may be selected depending on various factors such as the volume of sequencing desired, the type of labels employed, the number of different adaptors used within each library construct, the number of bases being queried per cycle, how the DNBs are attached to the sites on the surface of the array chip, the desired speed of sequencing operations, signal detection approaches, and the like.

The degenerate (e.g., 8-mer) probes can be labeled in a variety of ways, including the direct or indirect attachment of radioactive moieties, fluorescent moieties, colorimetric moieties, chemiluminescent moieties, fluorophores, and the like. Many comprehensive reviews of methodologies for labeling DNA and constructing DNA adaptors provide guidance applicable to constructing oligonucleotide probes of the present invention. Such reviews include Kricka (2002), Ann. Clin. Biochem., 39: 114-129, and Haugland (2006); Handbook of Fluorescent Probes and Research Chemicals, 10th Ed. (Invitrogen/Molecular Probes, Inc., Eugene); Keller and Manak (1993), DNA Probes, 2nd Ed. (Stockton Press, New York, 1993); and Eckstein (1991), Ed., Oligonucleotides and Analogues: A Practical Approach (IRL Press, Oxford); and the like.

Imaging acquisition may be performed by methods known in the art, such as use of the commercial imaging package Metamorph. Data extraction may be performed by logic including a series of binaries written in, e.g., C/C++, and base-calling and read-mapping may be performed by a series of Matlab and Perl scripts. As described above, for each base in a target nucleic acid to be queried (for example, for 12 bases, reading 6 bases in from both the 5' and 3' ends of each target nucleic acid portion of each DNB), a hybridization reaction, a ligation reaction, imaging, and a primer stripping reaction is performed. To determine the identity of each DNB attached in a site on an array chip at a given position, after performing the biological sequencing reactions, each field of view ("frame") is imaged with four different wavelengths corresponding to the four fluorescent, e.g., 8-mers used. During the process of imaging, as described herein Moiré averaging based on the information encoded as the sites in the track regions of the array chip may be used to align the camera pixels of the imagining instrument with the sites on the array chip. The images from each cycle may be saved in a cycle directory, where the number of images is four times the number of frames (for example, if a four-fluorophore technique is employed). Cycle image data may then be saved into a directory structure organized for downstream processing.

Data extraction typically requires two types of image data: bright field images to demarcate the positions of all DNBs in the array chip; and sets of fluorescence images acquired during each sequencing cycle. The data extraction software identifies all objects with the bright field images, then for each such object, computes an average fluorescence value for each sequencing cycle. For any given cycle, there are four datapoints, corresponding to the four images taken at different wavelengths to query whether that base is an A, G, C or T. These raw base-calls are consolidated, yielding a discontinuous, mate-paired sequencing read for each DNB. Each such mate-paired read includes two arms each representing a sequence of about 35 bp, where the two arms have been extracted from the two ends of a DNA fragment that may have been 200-500 bp in length; thus, the two aims of a mate-paired read may be separated by about 200-300 bp apart with respect to the underlying DNA fragment. The extracted sequencing reads may then be matched against a reference genome by using various techniques and algorithms that can be performed by one or more computer systems.

While the present invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the claims and their equivalents that issue from the present application. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. A chip for assays comprising:
    a solid planar substrate;
    a two-dimensional array of experiment sites on the substrate, characterized as having a uniform distance between adjacent experiment sites in each row and between adjacent experiment sites in each column;
    a linear array of alignment sites on the substrate, characterized as having a uniform distance between adjacent alignment sites; and
    a site free band separating the two-dimensional array and the linear array, the site free band having a width that is greater than the uniform distance between adjacent experiment sites in the two dimensional array;
    wherein experiment sites in the two dimensional array and alignment sites in the linear array have a surface that is chemically functionalized to bind and retain nucleic acid macromolecules;
    wherein outside the experiment sites and the alignment sites, the substrate has a surface that resists binding of nucleic acid macromolecules; and
    wherein the uniform distance between sites in the linear array is a non-integral multiple of the uniform distance between the rows and between the columns in the two-dimensional array.

2. An array chip according to claim 1 aligned with a digital camera such that each experiment site on the array chip is aligned with a single pixel of the digital camera.

3. The chip of claim 1, wherein the experiment sites in the two dimensional array are arranged in a checkerboard pattern.

4. The chip of claim 1, wherein selected ones of the alignment sites are deleted in accordance with a preselected pattern.

5. The chip of claim 1, wherein selected ones of the alignment sites are deleted in accordance with a pseudo-random pattern.

6. The chip of claim 1, wherein said experiment sites and said alignment sites are chemically functionalized to bind and retain DNA nanoballs.

7. The chip of claim 1, wherein
    the two-dimensional array has a longer edge and a shorter edge, and the linear array is oriented parallel to the longer edge.

8. The chip of claim 1, wherein
    the two-dimensional array has a longer edge and a shorter edge, and the linear array is oriented parallel to the shorter edge.

9. The chip of claim 1, wherein the surface further comprises a second linear array of alignment sites separated from the two dimensional array by a site-free band, wherein the second linear array is perpendicular to the first linear array.

10. The chip of claim 1, wherein the nucleic acid macromolecules are nucleic acid amplicons.

11. The chip of claim 1, configured so that when the experiment sites in the patterned array have nucleic acid amplicons attached thereto, at least 90% of the nucleic acid macromolecules on the experimental sites can be aligned and imaged for discrete analysis.

12. The chip of claim 1, wherein experiment sites in the two dimensional array and alignment sites in the linear array have nucleic acid macromolecules attached thereto.

13. The chip of claim 12, wherein the nucleic acid macromolecules are attached to the experiment sites and the alignment sites non-covalently.

14. The chip of claim 12, wherein the nucleic acid macromolecules have fluorophore-labeled probes hybridized thereto that are configured for determining sequences of the macromolecules.

15. The chip of claim 1, comprising a plurality of said two-dimensional arrays on the planar substrate separated from each other by a dividing space that includes a site free band having a width that is greater than the uniform distance between adjacent experiment sites in the two dimensional arrays.

16. The chip of claim 15, wherein the dividing space includes a linear array of alignment sites with a site free band on either side.

17. The chip of claim 15, wherein said two-dimensional arrays are arranged in a plurality of columns and a plurality of rows.

18. The chip of claim 15, comprising at least 16 of said two-dimensional arrays.

19. The chip of claim 12, wherein nucleic acid macromolecules in the experimental and the alignment sites are each labeled with one of at least four different fluorophores, each fluorophore indicating a different nucleotide base.

* * * * *